(12) United States Patent
Pariza et al.

(10) Patent No.: US 6,482,434 B1
(45) Date of Patent: Nov. 19, 2002

(54) METHOD FOR REDUCING ADVERSE EFFECTS OF A WEIGHT LOSS REGIMEN

(75) Inventors: Michael W. Pariza, Madison, WI (US); Richard L. Atkinson, Jr., Fitchburg, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 0 days.

(21) Appl. No.: 09/542,577

(22) Filed: Apr. 4, 2000

(51) Int. Cl.[7] .......................... A61K 9/20; A61K 9/22; A61K 9/26

(52) U.S. Cl. ................ 424/465; 424/464; 424/468; 424/469; 424/470

(58) Field of Search ................ 424/465, 464, 424/468, 470, 469; 514/560

(56) References Cited

U.S. PATENT DOCUMENTS

| | | | |
|---|---|---|---|
| 4,328,243 A | * | 5/1982 | Horrobin et al. ........... 424/301 |
| 5,430,066 A | * | 7/1995 | Cook et al. ................. 514/558 |
| 5,444,054 A | * | 8/1995 | Garleb et al. ................ 514/54 |
| 5,554,646 A | | 9/1996 | Cook et al. |
| 5,585,400 A | | 12/1996 | Cook et al. |
| 5,814,663 A | | 9/1998 | Cook et al. |
| 5,856,149 A | * | 1/1999 | Pariza et al. ................. 435/134 |
| 5,919,451 A | | 7/1999 | Cook et al. |
| 6,020,378 A | | 2/2000 | Cook et al. |

OTHER PUBLICATIONS

Beerthuis et al., "Synthesis of a Series of Polyunsaturated Fatty Acids, Their Potencies as Essential Fatty Acids and as Precursors of Prostaglandins", *Recl. Trav. Chim. Pays–Bas* 90:943–960 (1971).

Fretland et al., "The Long Duration in vivo, Inhibition of Prostaglandin Synthetase by 2–Methyl–8CIS–12–Trans–14–CIS–Eicosatrien Oic Acid", *Biochem. Pharmacol.* 34(12):2103–2107 (1985).

Nugteren, D.H., "Inhibition of Prostaglandin Biosynthesis by 8CIS, 12Trans, 14CIS–Eicosatrienoic Acid and 5CIS, 8CIS, 12Trans, 14CIS Eicosatetraenoic Acid", *Biochim. Biophys. Acta* 210(1):171–176 (1970).

Nugteren et al., "Naturally Occurring Conjugated Octadecatrienoic Acids are Strong Inhibitors of Prostaglandin Biosynthesis", *Prostaglandins* 33(3):403–417 (1987).

* cited by examiner

Primary Examiner—Thurman K. Page
Assistant Examiner—Rachel M. Bennett
(74) Attorney, Agent, or Firm—Quarles & Brady LLP

(57) ABSTRACT

A method for reducing certain effects associated with a negative calorie balance in a human includes the step of administering conjugated linoleic acid to a human in an amount effective to reduce at least one of the effects.

2 Claims, No Drawings

METHOD FOR REDUCING ADVERSE EFFECTS OF A WEIGHT LOSS REGIMEN

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The percentage of persons whose health is jeopardized by too much weight is increasing. Evidence suggests that body weight is multifactorial in origin, reflecting inherited, environmental, cultural, socioeconomic, and psychological conditions. Increasing evidence suggests that being overweight is not a simple problem of will power, as is sometimes implied, but is a complex disorder of appetite regulation and energy metabolism. Many persons have a chronic tendency for becoming overweight that needs lifelong attention. Strategies employed to lose weight include caloric restriction, exercise, behavior modification, drugs, or combinations thereof, with or without medial supervision. Some attempts may be successful in the short term, but often the weight lost is regained.. Efforts to lose weight voluntarily encompass a continuum of individuals including those of normal or low weight who wish to lose weight for cultural, social, or psychological reasons to severely overweight persons who suffer resulting adverse medical consequences.

The success of a weight loss program is highly variable. Psychological factors play a role both in the maintenance of weight and in the success of any weight loss program. Participants can reduce baseline depression and anxiety associated with a desire to reduce weight, but only if they successfully lose weight. Little is known about the emotional impact of lesser degrees of success or of failure, but it is assumed that improved self-esteem is instrumental in the overall success of the program. There is also increasing evidence that mildly to moderately overweight women who are dieting may be at risk for binge-eating without vomiting and purging.

An individual's response to a weight loss strategy is unpredictable. Success rates can be expected to vary according to initial weight, the length of the treatment period, the magnitude of weight loss desired, and the motivation for wanting to lose weight. The effectiveness of unsupervised efforts to lose weight is difficult to judge because of limited data on strategies, compliance, and follow-up. Surveys indicate that many overweight people have tried to lose weight on multiple occasions; because many of these persons presumably are using these unsupervised strategies, their long-term success rates may be low.

In general, successful programs are those based on realistic goals that involve a negative calorie balance (caloric deficit) leading to a slow, steady weight loss. Success requires a regimen that can be adhered to long enough to reach the goal. Developing new weight reduction practices that could lead to a lifetime of weight control is also important. Other attributes of successful programs involve preparing the person to deal with high-risk emotional and social situations, self-monitor progress, solve problems, reduce stress, and maintain continual professional contact. Barriers to success include lack of feelings of self-efficacy, failure to lose weight early, premature termination of diet modifications or exercise or both, and lack of social and professional support. Serious underlying social or psychological problems such as depression also can be barriers to success.

It would be useful to have a treatment that would attenuate the negative psychological and physical aspects of a weight control regimen.

BRIEF SUMMARY OF THE INVENTION

The present invention is summarized in that a method for reducing at least one adverse effect of a negative calorie balance in a human includes the steps of administering to the human an amount of conjugated linoleic acid (CLA) effective to reduce at least one negative effect selected from the group consisting of a skin rash, a gastrointestinal problem, a negative mood effect, and a cognitive or central nervous system (CNS) side effect.

It is an object of the present invention to decrease one or more adverse effects of a negative calorie balance in a human.

It is another object of the invention to facilitate weight loss in a human for whom the adverse effects of weight reduction brought about by negative calorie balance pose a significant impediment to successful weight reduction.

It is an advantage of the present invention that the method for reducing adverse effects is effective without regard to the means by which a negative calorie balance is achieved.

Other objects, advantages, and features of the invention will become apparent upon consideration of the following detailed description.

BRIEF DESCRIPTION OF THE SEVERAL VIEWS OF THE DRAWINGS

Not applicable.

DETAILED DESCRIPTION OF THE INVENTION

A human can be subjected to a negative calorie balance in any of a number of ways. In its most basic form, the term "negative calorie balance" refers to a situation in which a human burns more calories than he or she takes in. A human can take in calories by, e.g., oral ingestion, by gastrointestinal feeding, or by intravenous delivery. Humans can achieve a negative calorie balance by, e.g., reducing food intake, either with or without pharmaceutical assistance, or by increasing calorie-burning activity.

As will become apparent from the working example, reductions in adverse effects were observed in a double-blind controlled study of subjects who received either conjugated linoleic acid (CLA) or a vegetable oil placebo. Subjects were asked to self-report any physiological changes noted during the course of treatment. As the data below demonstrate, CLA is shown to have a statistically significant effect on certain conditions, broadly characterized as reduced skin rash, gastrointestinal problems, reduced negative mood, and reduced cognitive/CNS side effects.

CLA can contain various isomers of conjugated linoleic acid (the structures of which are known to the art) or can be a preparation of a single isomer. Distinct isomers can have distinct effects on various body systems (see U.S. Pat. No. 6,020,378, incorporated herein by reference as if set forth herein in its entirety). Other recent issued US patents relating to use of CLA include U.S. Pat. Nos. 5,919,451; 5,914,346; and 5,855,917, each of which is incorporated herein by reference as if set forth herein in its entirety. The particular effects of individual isomers on the adverse effects of a weight loss regimen are not well characterized. CLA administered in the method can contain about 1% to 99% trans-10, cis-12 CLA and approximately 99% to 1% cis-9, trans-10 CLA. CLA can be administered as a dietary supplement or in food, as free fatty acids, or as active esters (e.g., triglycerides, diglycerides, or monoglycerides), as active salts thereof, or in any other biologically active form. The CLA can be administered by any route that results in delivery of biologically active material to the recipient, including, but not limited to, oral, intravenous or intramuscular administration. The CLA can be formulated with a carrier to form a composition for administration in the method. An effective CLA-containing composition for oral administration is Tonalin-90, which is a mixture of about 90% CLA isomers (approximately 43.5% trans-10, cis-12 CLA, 42% cis-9, trans-11 CLA, 2% trans-trans CLA isomers, and 1.5% other CLA isomers). On oral administration, an effective amount of CLA is between about 1 and 10 grams per day, preferably 2 to 5 grams per day, although greater or lesser amounts may also be effective. The effective amount can also depend upon the CLA isomer ratio in the administered composition.

EXAMPLE

Human subjects were placed on a weight loss regimen of reduced calorie intake and increased exercise. The regimen was such that each subject achieved a negative calorie balance. Eighty-two subjects were in the study when it began and eighty remained in the study when the treatments were randomized. All subjects received a placebo for two weeks. After this stage, 71 subjects remained in the study. Using a double-blind protocol, thirty-five of the subjects then remaining in the study were administered Tonalin-90 CLA and thirty-six were administered a vegetable oil placebo. Subjects were asked to take one pill with each meal (3 grams of Tonalin-90 per day, for a total dose of about 2.7 grams of CLA per day).

Visits occurred at 2 week intervals. Subjects were asked about physiological changes or symptoms in a self-reporting questionnaire-style format. For each symptom, subjects were asked to report whether they experienced or did not experience the symptom. Tables 1–6 report the data from the double-blind protocol. The data presented in the (+) and (−) columns indicates the number of subjects in the test and control groups that reported or did not report the indicated symptom at some time during the study. The calculations columns report the CHI-square ranges for each variable. The p-value reported from the CHI-squared analysis of the data report the statistical significance of each observation. A p-value of less than 0.05 is considered statistically significant; a p-value of between 0.05 and 0.1 indicates a trend. In this study, effects having a p-value of less than 0.1 are considered to be meaningful and of interest by the inventors. Table 7 summarizes positive effects of CLA having a p-value of less than 0.1.

The present invention is not intended to be limited to the preceding embodiments or to the working example, but rather encompasses all modifications and variations that fall within the scope of the appended claims.

TABLE 1

CHI-SQUARED ANALYSIS: GI side effects-CLA vs Placebo

|  | (+) | (−) | calculations: | |
|---|---|---|---|---|
| Abdominal Pain | | | | |
| CLA | 7 | 28 | 8.380 | 26.620 |
| PLACEBO | 10 | 26 | 8.620 | 27.380 |
| | | | p-val = | 0.443 |
| Constipation | | | | |
| CLA | 2 | 33 | 3.451 | 31.549 |
| PLACEBO | 5 | 31 | 3.549 | 32.451 |
| | | | p-val = | 0.248 |
| Diarrhea | | | | |
| CLA | 8 | 27 | 12.324 | 22.676 |
| PLACEBO | 17 | 19 | 12.676 | 23.324 |
| | | | p-val = | 0.032 |
| Dry Mouth | | | | |
| CLA | 4 | 31 | 4.930 | 30.070 |
| PLACEBO | 6 | 30 | 5.070 | 30.930 |
| | | | p-val = | 0.526 |
| Gall Bladder Prob | | | | |
| CLA | 1 | 34 | 0.493 | 34.507 |
| PLACEBO | 0 | 36 | 0.507 | 34.493 |
| | | | p-val = | 0.307 |
| Nausea/Vomiting | | | | |
| CLA | 8 | 27 | 11.338 | 23.662 |
| PLACEBO | 15 | 21 | 11.662 | 24.338 |
| | | | p-val = | 0.090 |
| Heartburn | | | | |
| CLA | 6 | 29 | 6.901 | 28.099 |
| PLACEBO | 8 | 28 | 7.099 | 28.901 |
| | | | p-val = | 0.591 |
| Total GI Symptoms | | | | |
| CLA | 36 | 209 | 47.817 | 197.183 |
| PLACEBO | 61 | 191 | 49.183 | 202.817 |
| | | | p-val = | 0.007 |

TABLE 2

CHI-SQUARED ANALYSIS: Negative Mood side effects-CLA vs Placebo

|  | (+) | (−) | calculations: | |
|---|---|---|---|---|
| Lower Sex Drive | | | | |
| CLA | 0 | 35 | 0.493 | 34.507 |
| PLACEBO | 1 | 35 | 0.507 | 35.493 |
| | | | p-val = | 0.321 |
| Anxiety | | | | |
| CLA | 4 | 31 | 5.423 | 29.577 |
| PLACEBO | 7 | 29 | 5.577 | 30.423 |
| | | | p-val = | 0.351 |
| Depression | | | | |
| CLA | 3 | 32 | 5.915 | 29.085 |
| PLACEBO | 9 | 27 | 6.085 | 29.915 |
| | | | p-val = | 0.065 |
| Irritability/Anger | | | | |
| CLA | 5 | 30 | 6.408 | 28.592 |
| PLACEBO | 8 | 28 | 6.592 | 29.408 |
| | | | p-val = | 0.387 |
| Nervousness | | | | |
| CLA | 3 | 32 | 1.972 | 33.028 |
| PLACEBO | 1 | 35 | 2.028 | 33.972 |
| | | | p-val = | 0.290 |

TABLE 2-continued

CHI-SQUARED ANALYSIS: Negative Mood side effects-CLA vs Placebo

|  | (+) | (−) | calculations: |  |
|---|---|---|---|---|
| Binge Eating |  |  |  |  |
| CLA | 1 | 34 | 2.958 | 32.042 |
| PLACEBO | 5 | 31 | 3.042 | 32.958 |
|  |  |  | p-val = | 0.095 |
| Total Neg Mood Symptoms |  |  |  |  |
| CLA | 16 | 194 | 23.169 | 186.831 |
| PLACEBO | 31 | 185 | 23.831 | 192.169 |
|  |  |  | p-val = | 0.027 |

TABLE 3

CHI-SQUARED ANALYSIS: CV side effects-CLA vs. Placebo

|  | (+) | (−) | calculations: |  |
|---|---|---|---|---|
| Abnormal Heartbeat |  |  |  |  |
| CLA | 1 | 34 | 2.465 | 32.535 |
| PLACEBO | 4 | 32 | 2.535 | 33.465 |
|  |  |  | p-val = | 0.174 |
| Chest Pain |  |  |  |  |
| CLA | 2 | 33 | 1.479 | 33.521 |
| PLACEBO | 1 | 35 | 1.521 | 34.479 |
|  |  |  | p-val = | 0.539 |
| Short of Breath |  |  |  |  |
| CLA | 5 | 30 | 4.437 | 30.563 |
| PLACEBO | 4 | 32 | 4.563 | 31.437 |
|  |  |  | p-val = | 0.688 |
| Total CV Symptoms |  |  |  |  |
| CLA | 8 | 97 | 8.380 | 96.620 |
| PLACEBO | 9 | 99 | 8.620 | 99.380 |
|  |  |  | p-val = | 0.847 |

TABLE 4

CH-SQUARED ANALYSIS: Positive Mood side effects-CLA vs. Placebo

|  | (+) | (−) | calculations: |  |
|---|---|---|---|---|
| Higher Sex Drive |  |  |  |  |
| CLA | 1 | 34 | 0.493 | 34.507 |
| PLACEBO | 0 | 36 | 0.507 | 35.493 |
|  |  |  | p-val = | 0.307 |
| Elevated Mood |  |  |  |  |
| CLA | 2 | 33 | 2.465 | 32.535 |
| PLACEBO | 3 | 33 | 2.535 | 33.465 |
|  |  |  | p-val = | 0.666 |
| Total Pos Mood Symptoms |  |  |  |  |
| CLA | 3 | 67 | 2.958 | 67.042 |
| PLACEBO | 3 | 69 | 3.042 | 68.958 |
|  |  |  | p-val = | 0.972 |

TABLE 5

CHI-SQUARED ANALYSIS: Cognitive and CNS side effects-CLA vs. Placebo

|  | (+) | (−) | calculations: |  |
|---|---|---|---|---|
| Altered Sense Time |  |  |  |  |
| CLA | 1 | 34 | 0.986 | 34.014 |
| PLACEBO | 1 | 35 | 1.014 | 34.986 |
|  |  |  | p-val = | 0.984 |
| Loss Concentration |  |  |  |  |
| CLA | 2 | 33 | 3.451 | 31.549 |
| PLACEBO | 5 | 31 | 3.539 | 32.451 |
|  |  |  | p-val = | 0.248 |
| Blurred Vision |  |  |  |  |
| CLA | 2 | 33 | 2.958 | 32.042 |
| PLACEBO | 4 | 32 | 3.042 | 32.958 |
|  |  |  | p-val = | 0.414 |
| Dizziness |  |  |  |  |
| CLA | 3 | 32 | 6.901 | 28.099 |
| PLACEBO | 11 | 25 | 7.099 | 28.901 |
|  |  |  | p-val = | 0.020 |
| Headache |  |  |  |  |
| CLA | 17 | 18 | 16.761 | 18.239 |
| PLACEBO | 17 | 19 | 17.239 | 18.761 |
|  |  |  | p-val = | 0.909 |
| Memory Loss |  |  |  |  |
| CLA | 2 | 33 | 1.972 | 33.028 |
| PLACEBO | 2 | 34 | 2.028 | 33.972 |
|  |  |  | p-val = | 0.977 |
| Tremor |  |  |  |  |
| CLA | 1 | 34 | 0.493 | 34.507 |
| PLACEBO | 0 | 36 | 0.507 | 35.493 |
|  |  |  | p-val = | 0.307 |
| Drowsiness |  |  |  |  |
| CLA | 2 | 33 | 3.451 | 31.549 |
| PLACEBO | 5 | 31 | 3.549 | 32.451 |
|  |  |  | p-val = | 0.248 |
| Fatigue |  |  |  |  |
| CLA | 9 | 26 | 12.324 | 22.676 |
| PLACEBO | 16 | 20 | 12.676 | 23.324 |
|  |  |  | p-val = | 0.099 |
| Total Cognitive and CNS Symptoms |  |  |  |  |
| CLA | 39 | 276 | 49.296 | 265.704 |
| PLACEBO | 61 | 263 | 50.704 | 273.296 |
|  |  |  | p-val = | 0.025 |

TABLE 6

CHI-SQUARED ANALYSIS: Misc. side effects-CLA v. Placebo

|  | (+) | (−) | calculations: |  |
|---|---|---|---|---|
| Abnormal menses |  |  |  |  |
| CLA | 5 | 30 | 5.423 | 29.577 |
| PLACEBO | 6 | 30 | 5.577 | 30.423 |
|  |  |  | p-val = | 0.782 |
| Bruising |  |  |  |  |
| CLA | 1 | 34 | 2.465 | 32.535 |
| PLACEBO | 4 | 32 | 2.535 | 33.465 |
|  |  |  | p-val = | 0.174 |
| Hair Loss |  |  |  |  |
| CLA | 1 | 34 | 0.986 | 34.014 |
| PLACEBO | 1 | 35 | 1.014 | 34.986 |
|  |  |  | p-val = | 0.984 |

TABLE 6-continued

CHI-SQUARED ANALYSIS: Misc. side effects-CLA v. Placebo

|  | (+) | (−) | calculations: | |
|---|---|---|---|---|
| Leg Cramps | | | | |
| CLA | 4 | 31 | 3.451 | 31.549 |
| PLACEBO | 3 | 33 | 3.549 | 32.451 |
| | | | p-val = | 0.662 |
| Skin Rash | | | | |
| CLA | 0 | 35 | 1.479 | 33.521 |
| PLACEBO | 3 | 33 | 1.521 | 34.479 |
| | | | p-val = | 0.081 |
| Sweating | | | | |
| CLA | 4 | 31 | 4.930 | 30.070 |
| PLACEBO | 6 | 30 | 5.070 | 30.930 |
| | | | p-val = | 0.526 |
| Total Misc Symptoms | | | | |
| CLA | 15 | 195 | 18.732 | 191.268 |
| PLACEBO | 23 | 193 | 19.268 | 196.732 |
| | | | p-val = | 0.204 |

TABLE 7

SUMMARY OF SIDE EFFECTS REDUCED WITH CLA (P < 0.1)

|  | (+) | (−) | calculations: | |
|---|---|---|---|---|
| Skin Rash | | | | |
| CLA | 0 | 35 | 1.479 | 33.521 |
| PLACEBO | 3 | 33 | 1.521 | 34.479 |
| | | | p-val = | 0.081 |
| Diarrhea | | | | |
| CLA | 8 | 27 | 12.324 | 22.676 |
| PLACEBO | 17 | 19 | 12.676 | 23.324 |
| | | | p-val = | 0.032 |
| Nausea/Vomiting | | | | |
| CLA | 8 | 27 | 11.338 | 23.662 |
| PLACEBO | 15 | 21 | 11.662 | 24.338 |
| | | | p-val = | 0.090 |

TABLE 7-continued

SUMMARY OF SIDE EFFECTS REDUCED WITH CLA (P < 0.1)

|  | (+) | (−) | calculations: | |
|---|---|---|---|---|
| Depression | | | | |
| CLA | 3 | 32 | 5.915 | 29.085 |
| PLACEBO | 9 | 27 | 6.085 | 29.915 |
| | | | p-val = | 0.065 |
| Binge Eating | | | | |
| CLA | 1 | 34 | 2.958 | 32.042 |
| PLACEBO | 5 | 31 | 3.042 | 32.958 |
| | | | p-val = | 0.095 |
| Dizziness | | | | |
| CLA | 3 | 32 | 6.901 | 28.099 |
| PLACEBO | 11 | 25 | 7.099 | 28.901 |
| | | | p-val = | 0.020 |
| Fatigue | | | | |
| CLA | 9 | 26 | 12.324 | 22.676 |
| PLACEBO | 16 | 20 | 12.676 | 23.324 |
| | | | p-val = | 0.099 |

We claim:

1. A method for reducing an adverse effect on a human subject subjected to a negative calorie balance, the method comprising the step of:

administering an amount of conjugated linoleic acid effective to reduce an effect selected from the group consisting of a skin rash, a gastrointestinal problem, a negative mood, or a cognitive central nervous system side effect while maintaining the negative calorie balance.

2. A method as claimed in claim 1 wherein the effect reduced is selected from the group consisting of diarrhea, nausea, vomiting, depression, binge eating, dizziness, and fatigue.

* * * * *